United States Patent [19]

Ber

[11] Patent Number: 5,786,343
[45] Date of Patent: Jul. 28, 1998

[54] PHAGOCYTOSIS ACTIVATOR COMPOSITIONS AND THEIR USE

[75] Inventor: Leonid G. Ber, Houston, Tex.

[73] Assignee: ImmuDyne, Inc., Houston, Tex.

[21] Appl. No.: 811,584

[22] Filed: Mar. 5, 1997

[51] Int. Cl.$^6$ .................. A61K 31/715; A61K 31/375
[52] U.S. Cl. .................................. 514/54; 514/474
[58] Field of Search .................... 424/440; 514/54, 514/474

[56] References Cited

U.S. PATENT DOCUMENTS

| | | | |
|---|---|---|---|
| 3,793,052 | 2/1974 | Taylor | 117/36 |
| 3,862,336 | 1/1975 | Kofsky et al. | 416/1 |
| 3,889,007 | 6/1975 | Gunter et al. | 426/74 |
| 3,943,247 | 3/1976 | Komatsu et al. | 424/180 |
| 3,947,604 | 3/1976 | McGinley et al. | 426/573 |
| 4,072,567 | 2/1978 | Yokobayashi et al. | 195/63 |
| 4,138,479 | 2/1979 | Truscheit et al. | 424/88 |
| 4,343,784 | 8/1982 | Massot et al. | 424/45 |
| 4,438,200 | 3/1984 | Taubman et al. | 435/193 |
| 4,705,780 | 11/1987 | Massot et al. | 514/54 |
| 4,739,046 | 4/1988 | Di Luzio | 536/117 |
| 4,761,402 | 8/1988 | Williams et al. | 514/54 |
| 4,769,363 | 9/1988 | Misaki et al. | 514/54 |
| 4,818,752 | 4/1989 | Williams et al. | 514/54 |
| 4,833,131 | 5/1989 | Williams et al. | 514/54 |
| 4,891,220 | 1/1990 | Donzis | 424/88 |
| 4,900,722 | 2/1990 | Williams et al. | 514/54 |
| 4,935,250 | 6/1990 | Cox | 426/94 |
| 4,962,094 | 10/1990 | Jamas et al. | 514/54 |
| 4,965,347 | 10/1990 | Misaki et al. | 536/1.1 |
| 4,992,540 | 2/1991 | Jamas et al. | 536/123 |
| 5,032,401 | 7/1991 | Jamas et al. | 424/426 |
| 5,057,503 | 10/1991 | Czop et al. | 514/54 |
| 5,147,862 | 9/1992 | Nikl et al. | 514/54 |
| 5,183,667 | 2/1993 | Koch et al. | 424/474 |
| 5,189,028 | 2/1993 | Nikl et al. | 514/54 |
| 5,194,600 | 3/1993 | Bussey et al. | 536/23.74 |
| 5,217,740 | 6/1993 | Lanter | 426/573 |
| 5,223,491 | 6/1993 | Donzis | 514/54 |
| 5,250,436 | 10/1993 | Jamas et al. | 435/255.2 |
| 5,277,910 | 1/1994 | Hidvegi | 424/195.1 |
| 5,397,773 | 3/1995 | Donzis | 514/54 |
| 5,401,727 | 3/1995 | Rorstad et al. | 514/54 |
| 5,458,893 | 10/1995 | Smith | 426/18 |
| 5,474,926 | 12/1995 | Harman et al. | 435/200 |
| 5,504,079 | 4/1996 | James | 514/54 |
| 5,519,009 | 5/1996 | Donzis | 514/54 |
| 5,569,670 | 10/1996 | Weischer | 514/440 |
| 5,576,015 | 11/1996 | Donzis | 424/442 |

FOREIGN PATENT DOCUMENTS

| | | |
|---|---|---|
| 1242534 | 9/1989 | . |
| 2218615 | 8/1990 | . |
| 9003642 | 3/1992 | . |
| 6340701 | 12/1994 | . |
| 2063490 | 9/1992 | Canada . |
| 189959 | 8/1986 | European Pat. Off. . |
| 3835771 | 5/1989 | Germany . |
| 60116643 | 6/1985 | Japan . |
| 61070994 | 4/1986 | Japan . |
| 61146192 | 7/1986 | Japan . |
| 2199091 | 8/1990 | Japan . |
| 92-59509 | 2/1992 | Japan . |
| 94-238086 | 9/1994 | Japan . |
| 7051082 | 2/1995 | Japan . |
| 9104367 | 6/1991 | Rep. of Korea . |
| 2007152 | 2/1994 | Russian Federation . |
| 1397481 | 5/1988 | U.S.S.R. . |
| 90-4864625 | 6/1990 | U.S.S.R. . |
| 1591925 | 9/1990 | U.S.S.R. . |
| 1738852 | 6/1992 | U.S.S.R. . |
| WO90/12106 | 10/1990 | WIPO . |
| WO92/13896 | 8/1992 | WIPO . |
| WO93/22341 | 11/1993 | WIPO . |
| WO94/03498 | 2/1994 | WIPO . |
| WO95/04467 | 2/1995 | WIPO . |
| WO95/30022 | 11/1995 | WIPO . |
| WO96/20703 | 7/1996 | WIPO . |
| WO96/21363 | 7/1996 | WIPO . |
| WO96/26732 | 9/1996 | WIPO . |
| WO96/36341 | 11/1996 | WIPO . |
| WO97/02356 | 1/1997 | WIPO . |

OTHER PUBLICATIONS

Di Luzio, N.R., "Immunopharmacology of glucan: a broad spectrum enhancer of host defense mechanisms", Trends in Pharmacological Sciences, 4:344–347 (1983).

Schoenherr, W.D. et al, "MacroGard™-S—A New Concept for Feeding Starter Pigs", Research, H–102.

*Primary Examiner*—Gollamudi S. Kishore
*Attorney, Agent, or Firm*—Arnold, White & Durkee

[57] ABSTRACT

A phagocytosis-stimulating composition comprises, and preferably consists essentially of (a) a phagocytosis-stimulating substance, (b) ascorbic acid or a derivative thereof, and (c) a pharmaceutically acceptable carrier. The phagocytosis-stimulating substance suitably can be a yeast cell wall extract, such as beta-(1,3)-D-glucan. The compositions can be administered to animals to stimulate phagocytosis. The composition enhances and prolongs the stimulation of phagocytosis, by supplying ascorbic acid or an ascorbate to help replenish the ascorbate that has been depleted from the phagocytic cells such as macrophages. The composition has pharmaceutical, nutritional, and cosmetic uses, and can be used for prophylactic and therapeutic purposes.

9 Claims, No Drawings

PHAGOCYTOSIS ACTIVATOR COMPOSITIONS AND THEIR USE

BACKGROUND OF THE INVENTION

The present invention relates to compositions that can stimulate phagocytosis in animals such as mammals, birds, and aquatic animals, and also relates to the use of such compositions as nutritional supplements, dermatological preparations, and the like.

Glucan extracted from the cell walls of yeast is known to stimulate the immune system of animals, and specifically to stimulate phagocytosis. It is believed that glucan produces this effect by interacting with specific receptors located on macrophage cells.

Ascorbates are an essential cellular component of phagocytic cells such as macrophages and neutrophil polymorphonuclear leukocytes. These cells contain an intracellular concentration of ascorbate that is 10–40 times greater than its concentration in plasma. Depletion of ascorbate in phagocytic cells will negatively affect the cells' motility and their ability to perform their phagocytic function.

A need exists for improved phagocytosis-stimulating compositions, that can prolong the state of phagocytic cell activation, and enhance the ability of phagocytic cells to counteract physiological stress.

SUMMARY OF THE INVENTION

One aspect of the present invention concerns a phagocytosis-stimulating composition. The composition comprises, and preferably consists essentially of (a) a phagocytosis-stimulating substance, (b) ascorbic acid or a derivative thereof, and (c) a pharmaceutically acceptable carrier. The composition preferably consists essentially of about 0.0001–50 weight % of the phagocytosis-stimulating substance, about 0.1–99.99 weight % of ascorbic acid or a derivative thereof, and about 0.01–90 weight % of the carrier. The phagocytosis-stimulating substance suitably can be a yeast cell wall extract, such as a glucan. In one preferred embodiment, the phagocytosis-stimulating substance is primarily beta-(1,3)-D-glucan. "Primarily" in this context means that the phagocytosis-stimulating substance is a glucan that has more than about 50% (preferably more than about 75%, most preferably more than about 90%) beta-(1, 3)-D-glycosidic linkages. The ascorbic acid derivative is preferably a salt thereof, i.e., an ascorbate, with calcium ascorbate and ascorbyl palmitate being especially preferred examples.

If the composition is to be used for topical application rather than internal administration, then the composition can comprise, and preferably consists essentially of a phagocytosis-stimulating substance, ascorbic acid or a derivative thereof, and a dermatologically acceptable carrier. The distinction is that some carriers which are suitable for application to the skin might not necessarily be acceptable for internal use.

The compositions of the present invention can be used in methods of stimulating phagocytosis. The method comprises administering to an animal an amount of the composition that is effective to stimulate phagocytosis in the animal. The composition is preferably administered orally or topically, but might also be administered by injection. The animals with which the present invention can be used include mammals (including humans), birds, and aquatic animals such as fish.

Macrophages that have been stimulated, for example by the administration of a glucan, have been observed to exhibit a decrease in their intracellular ascorbate concentration. The present invention helps remedy this problem, and enhances and prolongs the stimulation of phagocytosis, by supplying ascorbic acid or an ascorbate to help replenish the ascorbate that has been depleted from the phagocytic cells such as macrophages. Further, because ascorbates are important vitamins for mammals, and are free radical scavengers, their inclusion in the composition of the present invention can have additional benefits, such as enhancing the ability to counteract or withstand infection, stress (including handling stress in mammals, birds, and aquatic species), and ionizing radiation.

The present invention in one sense provides a method of delivery of a system containing both a phagocytosis enhancing substance and ascorbic acid or any form of ascorbate.

The present invention has pharmaceutical, nutritional, and cosmetic uses. Oral or parenteral administration can result in enhanced immune system function, and enhanced growth and health of the animal. Topical administration can produce the same effects, and also can aid in reducing skin erythema, skin roughness, pigmentation, and irritation, for example from overexposure to UV radiation. The composition of the present invention can be used both for prophylactic and for therapeutic purposes.

DETAILED DESCRIPTION OF SPECIFIC EMBODIMENTS

One component of the present invention is a phagocytosis-stimulating substance, such as a yeast cell wall extract. Suitable examples include glucans from cell walls of *Saccharomyces cerevisiae* having beta-1,3-glycosidic linkages, or from other sources including other fungi and edible mushrooms, other polysaccharides with phagocytosis-enhancing properties, such as mannans (for example from Aloe Vera) and also more complex compound known to enhance phagocytosis such as plant extracts (Echinacea, Astragalus, Cats' Claw, Spirulina, and the like). Beta-1,3-D-glucan is available from ImmuDyne (Houston, Tex.) as Nayad.

Various processes for preparing glucans, and glucan compositions, are disclosed in U.S. Pat. Nos. 4,138,479, 4,891,220, 5,223,491, 5,397,773, 5,519,009, and 5,576,015. Those patents are incorporated here by reference.

Another component of the present invention is ascorbic acid or a derivative thereof. The ascorbic acid derivatives that are contemplated in the present invention are principally ascorbates that are suitable for ingestion by animal, with calcium ascorbate and ascorbyl palmitate being especially preferred. Ascorbic acid and/or ascorbates are available from numerous suppliers. Compounds that will metabolize or otherwise be converted to form ascorbic acid or ascorbates in vivo can also be used in the present invention.

The compositions of the present invention also include a pharmaceutically or dermatologically acceptable carrier. For compositions that will be administered orally, preferred carriers include maltodextrin, lactose, calcium lactate, and magnesium stearate. Compositions for oral administration will preferably take the form of a tablet, capsule, powder, suspension, solution, or syrup. For compositions that will be administered parenterally, preferred carriers include sterile water, saline solution, and glucose solution. For compositions that will be administered topically, preferred carriers include glycerin, butylene glycol, propylene glycol, and xanthan gum. Compositions of the present invention can further include additional pharmaceutically or dermatologically acceptable substances. The compositions of the present invention can be manufactured in these various forms by well-known means.

The dose administered of the phagocytosis-stimulating substance will vary depending on the mode of application and other circumstances. When the phagocytosis-stimulating substance is beta-(1,3)-D-glucan, the dosage administered to a mammal is preferably between approximately 0.0001 and 500 mg/kg of body weight/day, most preferably between about 0.01 and 10 mg/kg/day.

The present invention can be further understood from the following examples.

EXAMPLE 1

A suitable composition of the present invention for oral administration contains:

| | | |
|---|---|---|
| Beta-(1,3)-D-glucan | 7.5 mg | |
| Calcium ascorbate | 400 mg | |
| Magnesium stearate | 10 mg | |

EXAMPLE 2

A suitable composition of the present invention for topical administration contains:

| | | |
|---|---|---|
| water | 88.65% | (all percentages by weight) |
| Beta-(1,3)-D-glucan | 0.05% | |
| Ascorbyl palmitate | 10% | |
| Xanthan gum | 1% | |
| Methylparaben | 0.2% | |
| Propylparaben | 0.1% | |

The preceding description of specific embodiments of the present invention is not intended to be a complete list of every possible embodiment of the invention. Persons skilled in this field will recognize that modifications can be made to the specific embodiments described here that would be within the scope of the present invention.

What is claimed is:

1. A phagocytosis-stimulating composition that consists essentially of:
   a. about 0.0001–50 weight percent of a phagocytosis-stimulating substance that is primarily beta-(1,3)-D-glucan;
   b. ascorbic acid or a salt thereof; and
   c. a pharmaceutically acceptable carrier.

2. The composition of claim 1, where the ascorbic acid salt is selected from the group consisting of calcium ascorbate and ascorbyl palmitate.

3. A phagocytosis-stimulating composition that consists essentially of:
   a. about 0.0001–50 weight percent of a phagocytosis-stimulating substance that is primarily beta-(1,3)-D-glucan;
   b. ascorbic acid or a salt thereof; and
   c. a dermatologically acceptable carrier.

4. A method of stimulating phagocytosis, comprising administering to an animal a composition that consists essentially of about 0.001–50 weight percent of a phagocytosis-stimulating substance that is primarily beta-(1,3)-D-glucan, ascorbic acid or a salt thereof, and a pharmaceutically acceptable carrier, where the composition is administered in an amount effective to stimulate phagocytosis in the animal.

5. The method of claim 4, where the composition is administered to the animal orally.

6. The method of claim 4, where the composition is administered to the animal parenterally.

7. The method of claim 4, where the composition is administered to the animal topically.

8. The method of claim 4, where the ascorbic acid salt is selected from the group consisting of calcium ascorbate and ascorbyl palmitate.

9. The composition of claim 3, where the ascorbic acid salt is selected from the group consisting of calcium ascorbate and ascorbyl palmitate.

* * * * *